US009066768B2

(12) United States Patent
Weiner et al.

(10) Patent No.: US 9,066,768 B2
(45) Date of Patent: Jun. 30, 2015

(54) BONE PLATE HYBRID DEVICE

(75) Inventors: Lon S. Weiner, Rumson, NJ (US); John R. Pepper, Cheshire, CT (US)

(73) Assignee: Nextremity Solutions, Inc., Red Bank, NJ (US)

( * ) Notice: Subject to any disclaimer, the term of this patent is extended or adjusted under 35 U.S.C. 154(b) by 31 days.

(21) Appl. No.: 13/537,628

(22) Filed: Jun. 29, 2012
(Under 37 CFR 1.47)

(65) Prior Publication Data
US 2013/0006247 A1    Jan. 3, 2013

Related U.S. Application Data

(60) Provisional application No. 61/457,888, filed on Jun. 29, 2011.

(51) Int. Cl.
*A61B 17/80* (2006.01)
*A61B 17/68* (2006.01)
*A61B 17/86* (2006.01)

(52) U.S. Cl.
CPC ........... *A61B 17/809* (2013.01); *A61B 17/8033* (2013.01); *A61B 17/8042* (2013.01); *A61B 17/8052* (2013.01); *A61B 17/686* (2013.01); *A61B 17/8057* (2013.01); *A61B 17/8061* (2013.01); *A61B 17/8685* (2013.01)

(58) Field of Classification Search
CPC .. A61B 17/686; A61B 17/80; A61B 17/8033; A61B 17/8042; A61B 17/8052; A61B 17/8057; A61B 17/809; A61B 17/84; A61B 17/8685
USPC ......... 606/280–281, 286, 289, 291, 295, 297, 606/300–301, 319
See application file for complete search history.

(56) References Cited

U.S. PATENT DOCUMENTS

| 5,931,839 | A  | * | 8/1999  | Medoff .......................... 606/286 |
| 6,767,351 | B2 | * | 7/2004  | Orbay et al. .................. 606/287 |
| 7,229,445 | B2 | * | 6/2007  | Hayeck et al. ................. 606/70 |
| 7,717,945 | B2 | * | 5/2010  | Jensen et al. .................. 606/284 |
| 7,780,710 | B2 | * | 8/2010  | Orbay et al. .................. 606/286 |
| 8,439,918 | B2 | * | 5/2013  | Gelfand ......................... 606/74 |
| 8,545,539 | B2 | * | 10/2013 | Spencer ........................ 606/280 |
| 8,556,946 | B2 | * | 10/2013 | Prandi et al. .................. 606/286 |
| 2001/0011172 | A1 |  | 8/2001  | Orbay et al. |

(Continued)

FOREIGN PATENT DOCUMENTS

WO    WO 9402073 A1 *  2/1994    ........... A61B 17/064

OTHER PUBLICATIONS

International Preliminary Report on Patentability for international application No. PCT/US2012/044856, mailed on Jan. 16, 2014.

(Continued)

*Primary Examiner* — Larry E Waggle, Jr.
(74) *Attorney, Agent, or Firm* — Heslin Rothenberg Farley & Mesiti P.C.

(57) ABSTRACT

A method for joining of biological elements is disclosed. A plate is placed over a first segment and a second segment. The plate is attached to the first segment and the second segment. A dowel channel is drilled thru a dowel hole of the plate. A dowel is inserted into the dowel channel, wherein the dowel crosses a joining plane of the first segment and the second segment. A locking screw is placed on a top side of the dowel to lock the dowel in place.

51 Claims, 19 Drawing Sheets

(56) References Cited

U.S. PATENT DOCUMENTS

| | | |
|---|---|---|
| 2004/0030341 A1 | 2/2004 | Aeschlimann et al. |
| 2004/0210221 A1 | 10/2004 | Kozak et al. |
| 2010/0082028 A1* | 4/2010 | Hajianpour .................... 606/54 |
| 2011/0087229 A1 | 4/2011 | Kubiak et al. |
| 2011/0087295 A1 | 4/2011 | Kubiak et al. |

OTHER PUBLICATIONS

International Search Report for corresponding PCT application No. PCT/US2012/44856, mailed on Sep. 25, 2012.

* cited by examiner

BONE PLATE HYBRID DEVICE

CROSS-REFERENCE TO RELATED APPLICATIONS

The present application claims the benefit of U.S. Provisional Application Ser. No. 61/437,888 filed on 29 Jun. 2011, which is incorporated herein by reference in its entirety.

BACKGROUND OF THE INVENTION

Bone dowels have conventionally been used for spinal fusions. However, certain disadvantages are prevalent with the usage of bone dowels, such as low strength and risk of migration of the bone dowels. Bone dowels may also migrate if implanted in a loaded application, especially in the case of multiple bones or bone fragments. Crushed or damaged bones may also pose a problem.

Plates have been conventionally used to fix joints or for joint fusion. Plates are strong, but were meant only to be used with bone pastes. Bone pastes, or injectible bone growth enhancers could be used.

BRIEF SUMMARY OF THE INVENTION

In an embodiment, a method for joining of biological elements is disclosed. A plate is placed over a first segment and a second segment. The plate is attached to the first segment and the second segment. A dowel channel is drilled thru a dowel hole of the plate. A dowel is inserted into the dowel channel, wherein the dowel crosses a joining plane of the first segment and the second segment. A locking screw is placed on a top side of the dowel to lock the dowel in place.

In another embodiment, placing a plate over a first segment and a second segment comprises: placing a first plate portion of the plate over the first segment and a second plate portion of the plate over the second segment.

In another embodiment, attaching the plate to the first segment and the second segment comprises: inserting at least one screw into at least one hole of the plate; and screwing each of the at least one screw into a corresponding at least one hole of the plate such that the plate fastens to the first segment and the second segment.

In another embodiment, drilling a dowel channel thru a dowel hole of the plate comprises: inserting a drill bit thru the dowel hole of the plate; drilling the drill bit thru the dowel hole and into the first segment and the second segment to form a dowel channel, wherein the dowel channel crosses a joining plane of the first segment and the second segment; and removing the drill bit.

In another embodiment, inserting a dowel thru the dowel channel comprises: inserting the dowel thru the dowel channel until the dowel is implanted in both the first segment and the second segment.

In another embodiment, placing a locking screw on a top side of the dowel to lock the dowel in place comprises: placing the locking screw within a receiving chamber on the top side of the dowel; and screwing the locking screw into the dowel and the plate, wherein the locking screw engages with internal threads of the dowel hole to lock the dowel to the plate.

In another embodiment, the plate and dowel form a single constructive construct for joining after being locked into place.

In another embodiment, the first segment and the second segment are bone segments.

In another embodiment, the first segment and the second segment are joint segments.

In an embodiment, a system for joining of biological elements comprises a plate, at least one dowel, and at least one locking screw. The plate comprises a first portion comprising at least one hole and a second portion comprising at least one hole and at least one dowel hole. The at least one dowel is configured for insertion thru a dowel hole and into a dowel channel, wherein each dowel crosses a joining plane of a first segment and a second segment. The at least one locking screw is configured for mating with a top side of the at least one dowel to lock the at least one dowel in place.

In another embodiment, the first portion is placed over the first segment and the second portion is placed over the second segment.

In another embodiment, the system further comprises at least one screw for insertion into the at least one hole of the first portion and the second portion, wherein the at least one screw may be screwed into the at least one hole to fasten the plate to the first segment and the second segment.

In another embodiment, the system further comprises a drill bit for insertion thru the at least one dowel hole, wherein the drill bit may be drilled thru the at least one dowel hole and into the first segment and the second segment to form the dowel channel crossing a joining plane of the first segment and the second segment.

In another embodiment, each of the at least one dowel is inserted into a corresponding dowel channel until the at least one dowel is implanted in both the first segment and the second segment.

In another embodiment, the locking screw is placed into a receiving chamber on the top side of the at least one dowel, and the locking screw is configured to engage with internal threads of the at least one dowel hole to lock the at least one dowel to the plate.

In another embodiment, the plate and the at least one dowel form a single constructive construct for joining.

In another embodiment, the first segment and the second segment are bone segments.

In another embodiment, the first segment and the second segment are joint segments.

In an embodiment, an apparatus for joining of biological elements is disclosed. A first portion comprises at least one hole. A second portion comprises at least one hole and at least one dowel hole. Each of the at least one dowel hole is configured for receiving a dowel which is inserted into a dowel channel, wherein each dowel crosses a joining plane of a first segment and a second segment. Each of the at least one dowel hole comprises internal threads for engaging with at least one locking screw mating with a top side of the at least one dowel to lock the at least one dowel in place.

In another embodiment, the first portion is placed over the first segment and the second portion is placed over the second segment.

In another embodiment, the at least one hole of the first portion and the second portion are configured to receive at least one screw for insertion to fasten the plate to the first segment and the second segment.

In another embodiment, the at least one dowel hole is configured to receive a drill bit that may be drilled thru the at least one dowel hole and into the first segment and the second segment to form the dowel channel crossing a joining plane of the first segment and the second segment.

In another embodiment, the dowel channel of each of the at least one dowel hole is configured to receive a dowel that is implanted in both the first segment and the second segment.

In another embodiment, each of the at least one dowel hole comprises a receiving chamber on a top side of each of the at least one dowel.

In another embodiment, the plate and the at least one dowel form a single constructive construct for joining.

In another embodiment, the first segment and the second segment are bone segments.

In another embodiment, the first segment and the second segment are joint segments.

In another embodiment, the dowel is at least one of round, polygonal, or splined in cross section.

In another embodiment, the dowel is at least one of: bone, bone scaffold, mineral, ceramic, metal matrix, including stem cells, or including autologous material.

In an embodiment, a system for joining biological elements is disclosed. The system includes a plate and at least one dowel. The plate comprises a first portion comprising at least one retention element, and a second portion comprising at least one retention element at least one dowel hole. The at least one dowel is configured for insertion thru a dowel hole and into a dowel channel, wherein each dowel contacts both a first segment and a second segment.

In another embodiment, the at least one retention element is at least one of: a screw, a staple, or a flexible member. The flexible member may be a suture.

In another embodiment, the at least one dowel is retained in place within the dowel hole by mechanical contact with the plate.

In another embodiment, an anti-migration feature is configured for engagement with the dowel at the dowel hole. The anti-migration feature may be at least one of: a set screw, a spline interfering with at least a portion of a dowel, or a tapered fit.

In an embodiment, a system for joining biological elements is disclosed. The system comprises a plate and at least one dowel. The plate comprises a first portion comprising at least one retention feature and a second portion comprising at least one retention feature and at least one dowel contact point. The at least one dowel is configured for insertion thru a dowel channel, wherein each of the at least one dowel contacts a first segment and a second segment, and is held in place by a corresponding dowel contact point.

DETAILED DESCRIPTION OF THE INVENTION

The present disclosure is directed to methods, systems, and apparatuses for joining of biological elements. Joining of biological elements may include bone fusion and fixation, or joint fusion and fixation. As described herein, a plate may be applied to a first biological segment and a second biological segment to initially join and retain the joining of the segments. A dowel is inserted through the plate and into both segments, crossing the joining plane of the two segments, in order to provide additional stability to promote healing. Furthermore, the assembled hybrid plate including plate and dowel may serve as a biological scaffold. A locking screw may be placed atop the dowel to join the dowel to the plate in order to secure the dowel to the plate.

The assembled hybrid plate described herein may be used to join bones or joints in mammals. For example. Certain joints and bones that may be joined may include the talar navicular, calcaneal cubiod, ankle joint, talocalcaneal, medial malealor, shoulder, olecranon, distal femur, and tibial plateau fractures of a human.

Figure 1:
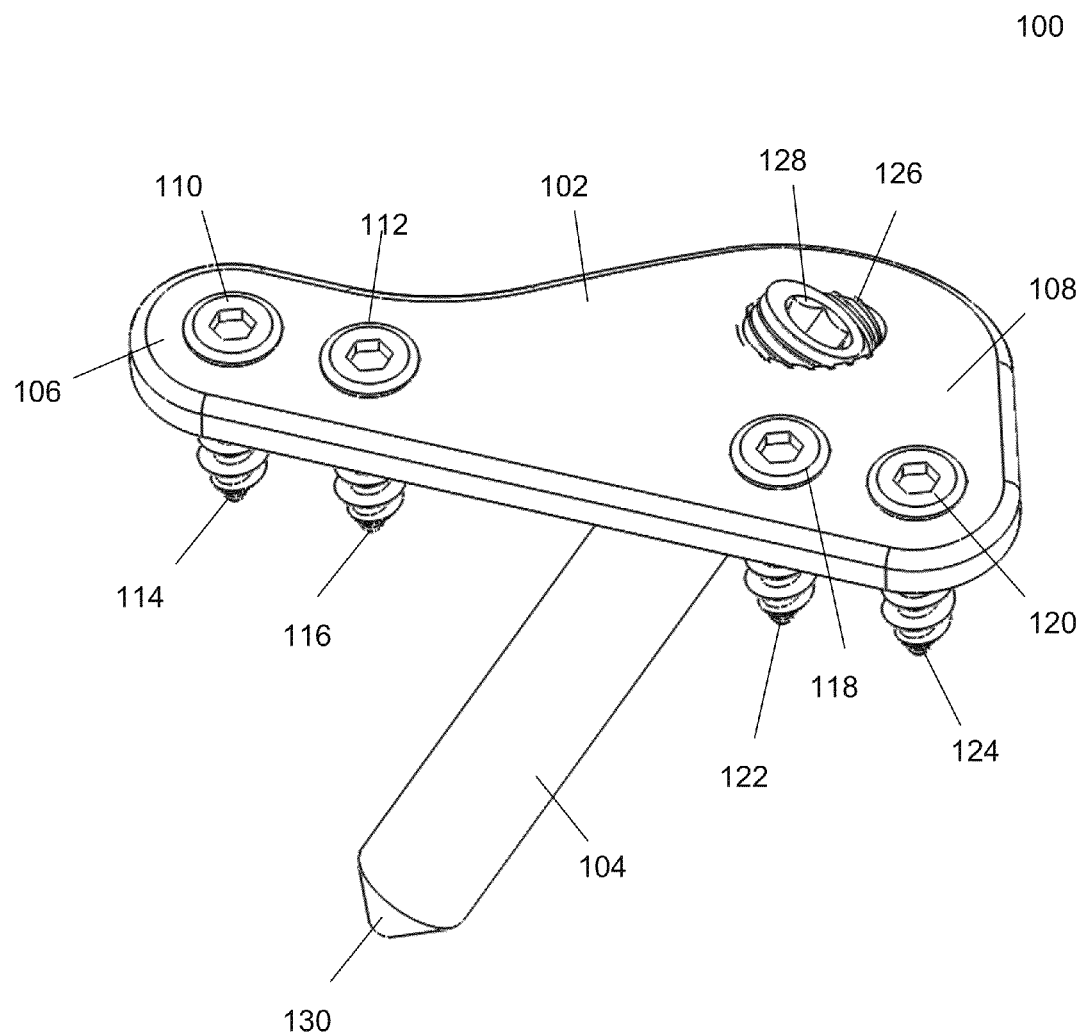
FIG. 1 depicts an isometric view of an assembled hybrid plate, in accordance with an embodiment of the present disclosure.

FIG. 1 depicts an isometric view of an assembled hybrid plate, in accordance with an embodiment of the present disclosure. Assembled hybrid plate 100 comprises plate 102 and dowel 104. Plate 102 includes a first plate portion 106 and a second plate portion 108. First plate portion 106 includes holes 110 and 112 for receiving screws 114 and 116. Second plate portion 108 includes holes 118 and 120 for receiving screws 122 and 124. Screws 114, 116, 122, and 124 are all adapted for attaching to biological segments, such as bones or joints. Second plate portion 108 further includes a dowel hole 126 for receiving dowel 104. Dowel hole 126 includes internal threads for engaging with a locking screw 128 which may be screwed into a top end of dowel 104.

While the exemplary embodiment shown by FIG. 1 and described herein depicts two holes on each plate portion and a single dowel hole on the second plate portion, plate 102 may be configured such that a greater or lesser amount of holes and dowel holes are present on the plate. As such, plate 102 may also be configured to receive more than one dowel through dowel holes with internal threads, and as a consequence, also receive a locking screw in one or more of the dowel holes.

Dowel 104, when inserted thru dowel hole 126, and into a dowel channel (not shown) that may be drilled through a first biological segment and a second biological segment, where dowel 104 crosses a joining plane of the first biological segment and the second biological segment. The joining plane represents the plane where the first biological segment and second biological segment are to be joined together. For example, the joining plane may be a fusion plane where two bone or joint segments are fused together. The joining plane may also be a fixation plane where two bone segments of a fractured bone are to be fixated. A bottom side 130 of dowel 104 may be pointed to facilitate insertion of dowel 104 through the first biological segment and the second biological segment.

Locking screw 128 engages or mates with a top side of dowel 104 in order to secure dowel 104 after dowel 104 has been inserted thru dowel hole 126. The top side of dowel 104 may include a receiving chamber specifically configured to receive locking screw 128. Although a receiving chamber is described, dowel 104 does not require a receiving chamber. To further secure dowel 104 to plate 102, locking screw 128 is screwed such that locking screw 128 engages internal threads of dowel hole 126 to lock dowel 104 into place with respect to plate 102. Locking screw 128 may also include a non-rotating feature to further prevent rotation of dowel 104 as locking screw 128 is applied.

First plate portion 106 may be placed over a first biological segment, while second plate portion 108 may be placed over a second biological segment. As a result, screws 114 and 116 secures or fastens a first biological segment to plate 102 and screws 122 and 124 secures or fastens a second biological segment to plate 102.

Prior to inserting dowel 104 thru dowel hole 126 and into the first biological segment and the second biological segment, a drill bit is inserted thru dowel hole 126. The drill bit may be drilled thru the first biological segment and the second biological segment to form a dowel channel, which crosses the joining plane of the first biological segment and the second biological segment. After drilling and removal of the drill bit, dowel 104 may be inserted thru dowel hole 126 and thru the dowel channel until dowel 104 is implanted in both the first biological segment and the second biological segment.

Once dowel 104 has been inserted and locked into place with locking screw 128, a single constructive construct or assembled hybrid plate 100 is formed for joining biological elements. The assembled hybrid plate 100 may further serve as a biological scaffold promoting cell growth. Thus, assembled hybrid plate 100 may be used not only for joining applications such as fusion and fixation, but also for tissue engineering in the promotion of tissue growth around the joined biological segments.

Plate 102 may take on any thickness, contour, or shape to be used for joining applications, as known to one of reasonable skill in the art. Dowel 104 may be 3.5, 4.0, 4.5, 5.0, 6.5 mm (conventional orthopaedic bone screw sizes), or any size that can be used for joining applications, as known to one of reasonable skill in the art. Dowel 104 may furthermore take on different configurations, such as being solid throughout, or being cannulated and including a cannula through dowel 104. Dowel 104 may further comprise materials including at least one of: bone, bone scaffold, mineral, metal matrix, including stem cells, including autologous material, ceramics, bio-absorbable scaffolds, trabecular metals, polymers, or autograft bones, as well as other materials used for joining applications, as known to one of reasonable skill in the art. The dowel may be at least one of round, polygonal, or splined in cross section.

Furthermore, as described above, as plate 102 may accommodate more than one dowel hole, plate 102 may also be configured for receiving a series of dowels. A greater amount of dowels provides a support matrix, which may be useful, for example, to support tibial plateau fractures.

Figure 2:
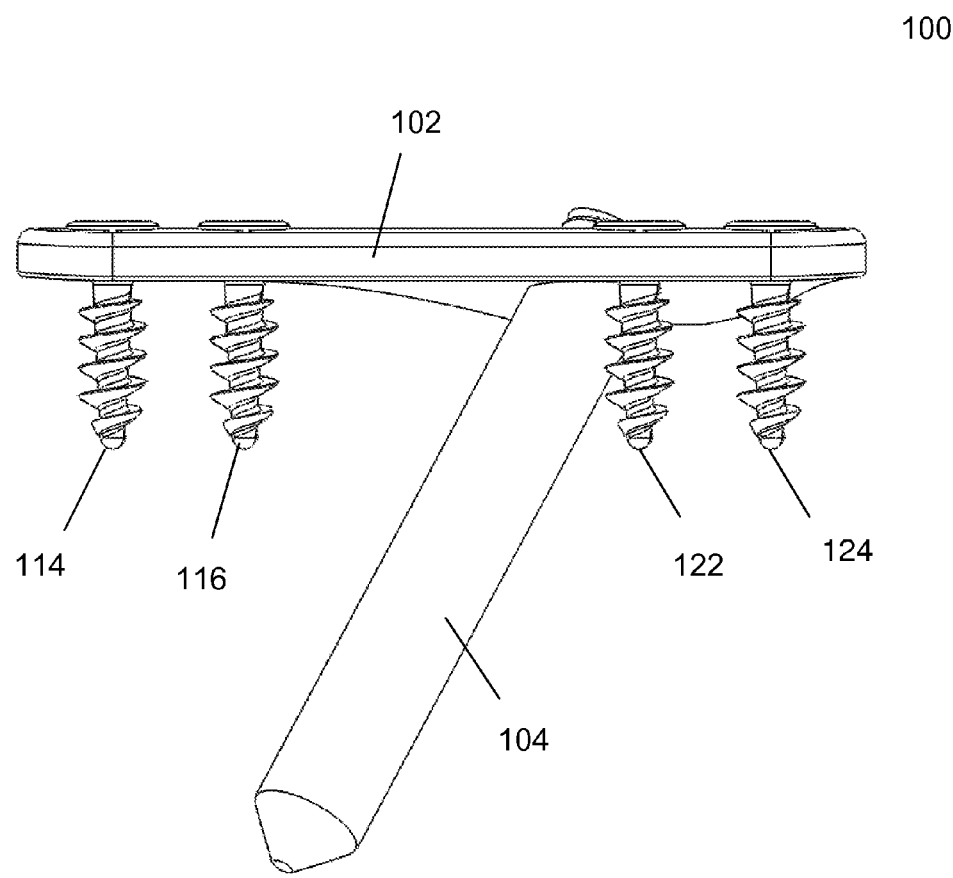
FIG. 2 depicts a side view of an assembled hybrid plate, in accordance with an embodiment of the present disclosure.

FIG. 2 depicts a side view of an assembled hybrid plate, in accordance with an embodiment of the present disclosure. A side view of assembled hybrid plate 100 is shown in FIG. 2. The side view presents an improved perspective of screws 114, 116, 122, and 124 which have been inserted thru holes of plate 102. Additionally, the oblique pathway of dowel 104 may be observed.

Figure 3:
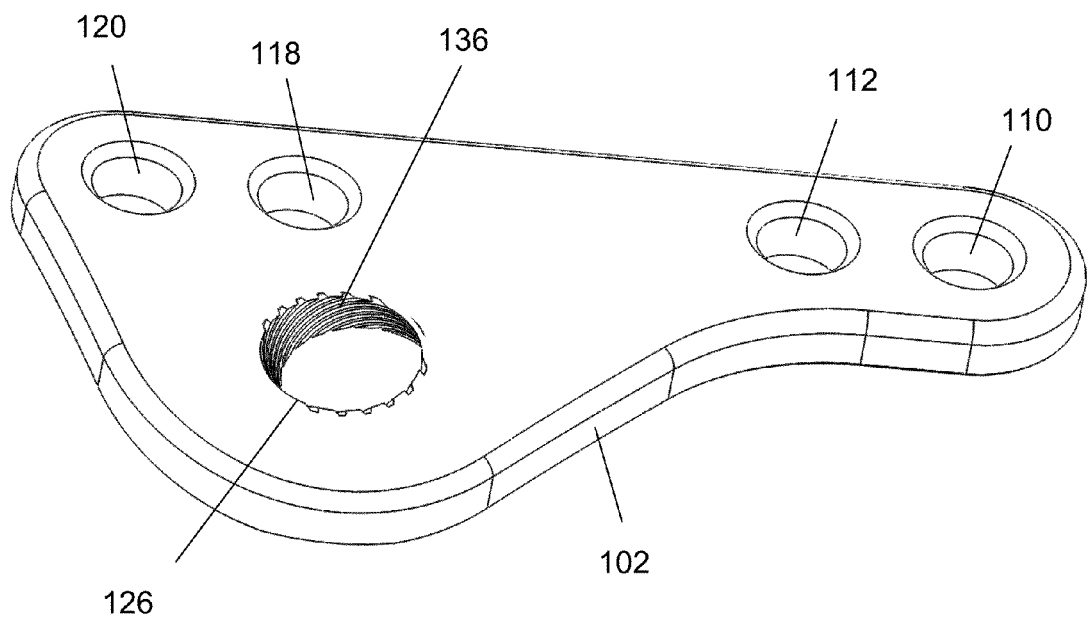
FIG. 3 depicts an isometric view of a plate showing internal threaded hole, in accordance with an embodiment of the present disclosure.

FIG. 3 depicts an isometric view of a plate showing internal threaded hole, in accordance with an embodiment of the present disclosure. As FIG. 3 depicts plate 102 without display of screws and dowel, holes 110, 112, 118, and 120 for receiving screws are more easily discernible. Internal threads 136 of dowel hole 126 are also viewable. Internal threads 136, as explained above, are adapted for engaging with locking screw 128 when locking screw is inserted into dowel 104 to lock dowel 104 and plate 102 into place and secure them with respect to one another.

Figure 4:
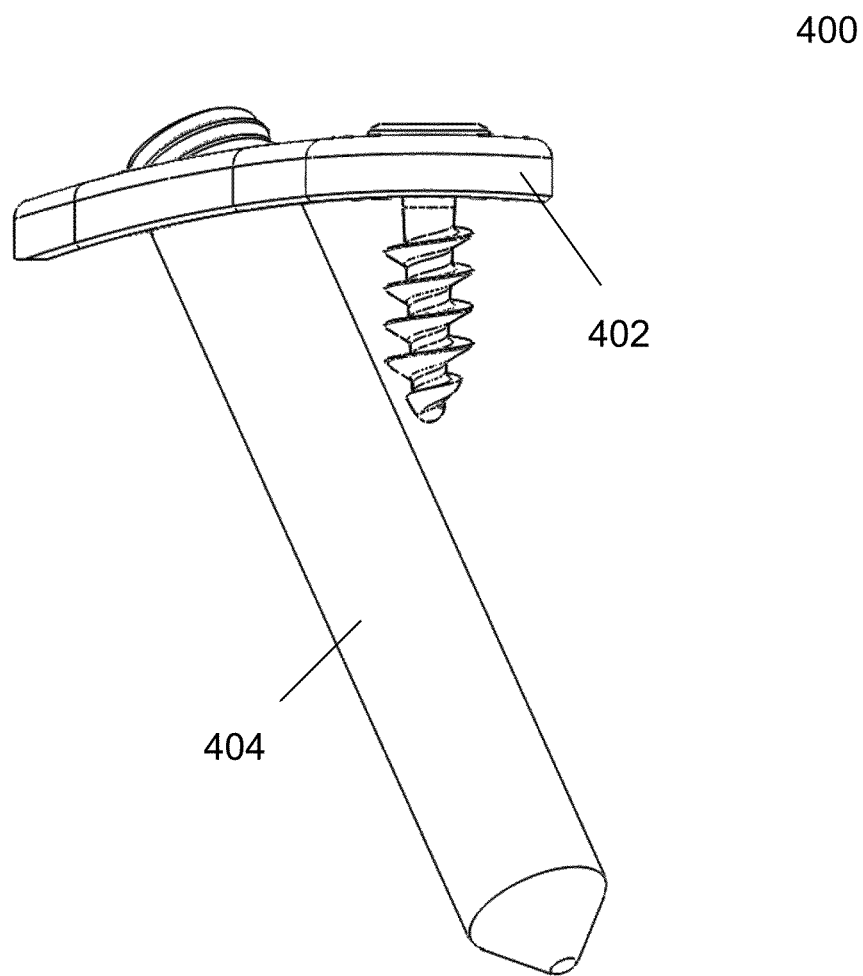
FIG. 4 depicts a perspective view of an assembled hybrid plate showing contouring to a bone surface, in accordance with an embodiment of the present disclosure.

FIG. 4 depicts a perspective view of an assembled hybrid plate showing contouring to a bone surface, in accordance with an embodiment of the present disclosure. FIG. 4 depicts an exemplary assembled hybrid plate 400 including plate 402 and dowel 404. Plate 402 is contoured to match a bone surface to which plate 402 and dowel 404 are being applied to. Dowel 404, for example, due to contouring of plate 402, is inserted at a different oblique pathway than dowel 104 as shown in FIGS. 1 and 2.

Figure 5:
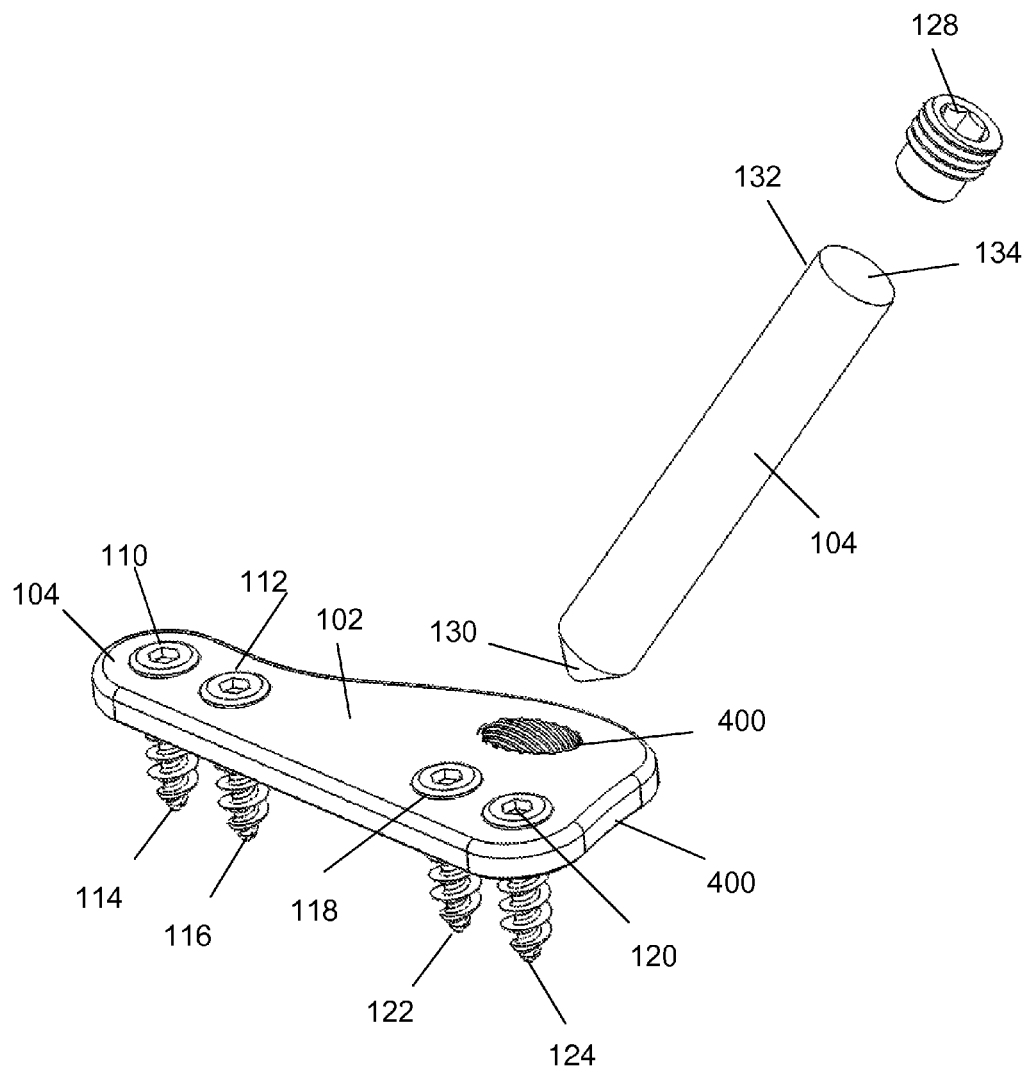
FIG. 5 depicts a perspective view of a plate after placement and prior to insertion of a dowel, in accordance with an embodiment of the present disclosure.

FIG. 5 depicts a perspective view of a plate after placement and prior to insertion of a dowel, in accordance with an embodiment of the present disclosure. Plate 102, as shown by FIG. 5, has already been applied to a first biological segment and a second biological segment. As such first plate portion 104 has been secured to a first biological segment by screws 114 and 116, and second plate portion 108 has been secured to a second biological segment by screws 122 and 124. However, dowel 104 has not yet been inserted thru dowel hole 126 and thru a drilled dowel channel.

Dowel 104 as shown includes a bottom side 130 and top side 132. Locking screw 128 is to be inserted into a receiving chamber 134 on top side 132 of dowel 104. Once locking screw 128 has been inserted into receiving chamber 134, dowel 104, now including locking screw 128 may be inserted thru dowel hole 126 and into the first biological segment and the second biological segment.

Figure 6:
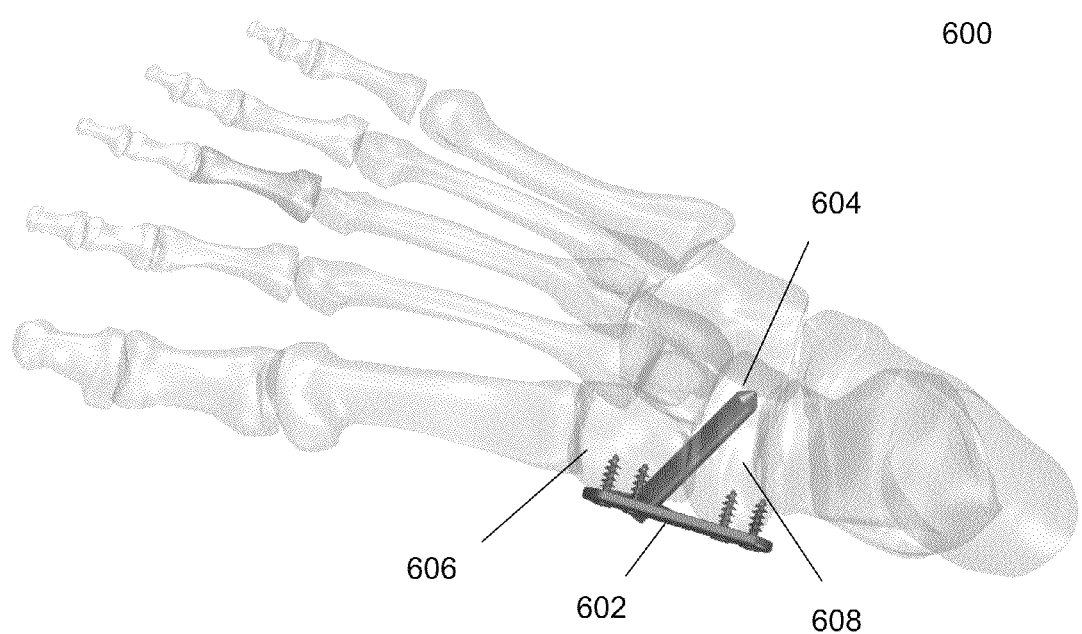
FIG. 6 depicts a joining site using an assembled hybrid plate, in accordance with an embodiment of the present disclosure.

FIG. 6 depicts a joining site using an assembled hybrid plate, in accordance with an embodiment of the present disclosure. FIG. 6 depicts a joining site of the talar and navicular using an assembled hybrid plate 600 in accordance with an embodiment of the present disclosure. Plate 602 and dowel 604 are already applied to bones 606 and 608. Plate 602 is held to bones 606 and 608 via screws, while dowel 604, as inserted is shown as crossing a joining plane of both bone 606 and 608.

Figure 7:
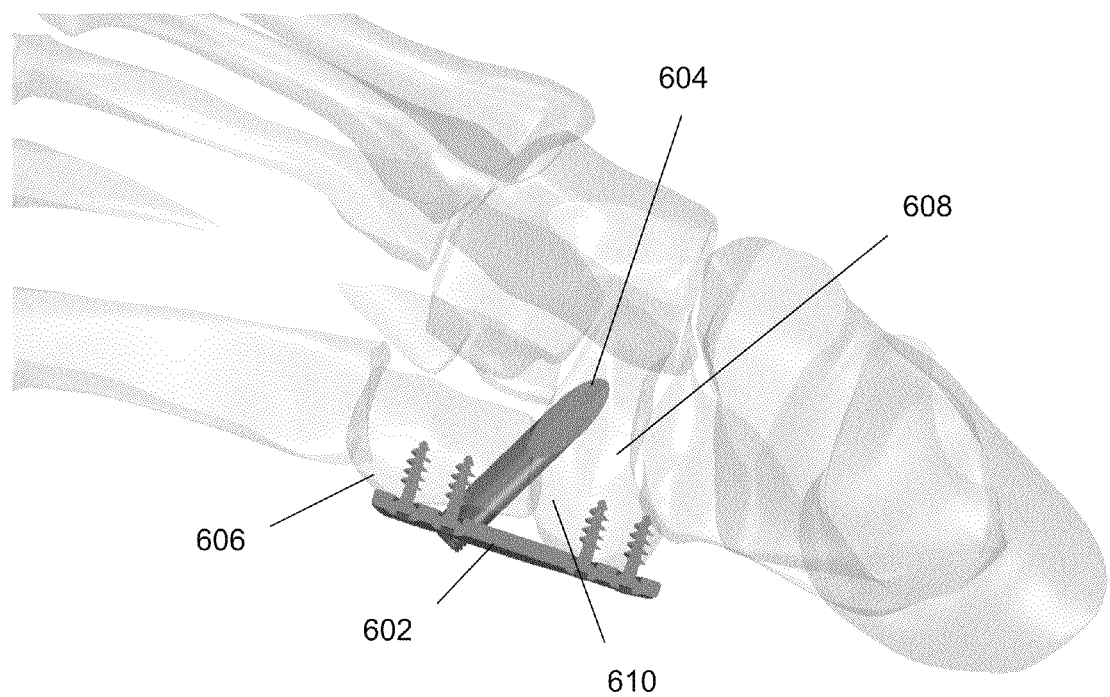
FIG. 7 depicts a joining site sectioned through screws, in accordance with an embodiment of the present disclosure.

FIG. 7 depicts a joining site sectioned through screws, in accordance with an embodiment of the present disclosure. FIG. 7 depicts assembled hybrid plate 600, as shown in FIG. 6, sectioned through screws. FIG. 7 provides a more detailed view of the joining site which is sectioned to show dowel 604 crossing a joining plane 610 of bones 606 and 608. Crossing of the joining plane 610 provides greater support and promotes further joining or healing of any defect suffered by bones 606 and 608, or any bones or joints which an assembled hybrid plate is applied to, in accordance with the embodiments described herein.

Figure 8:
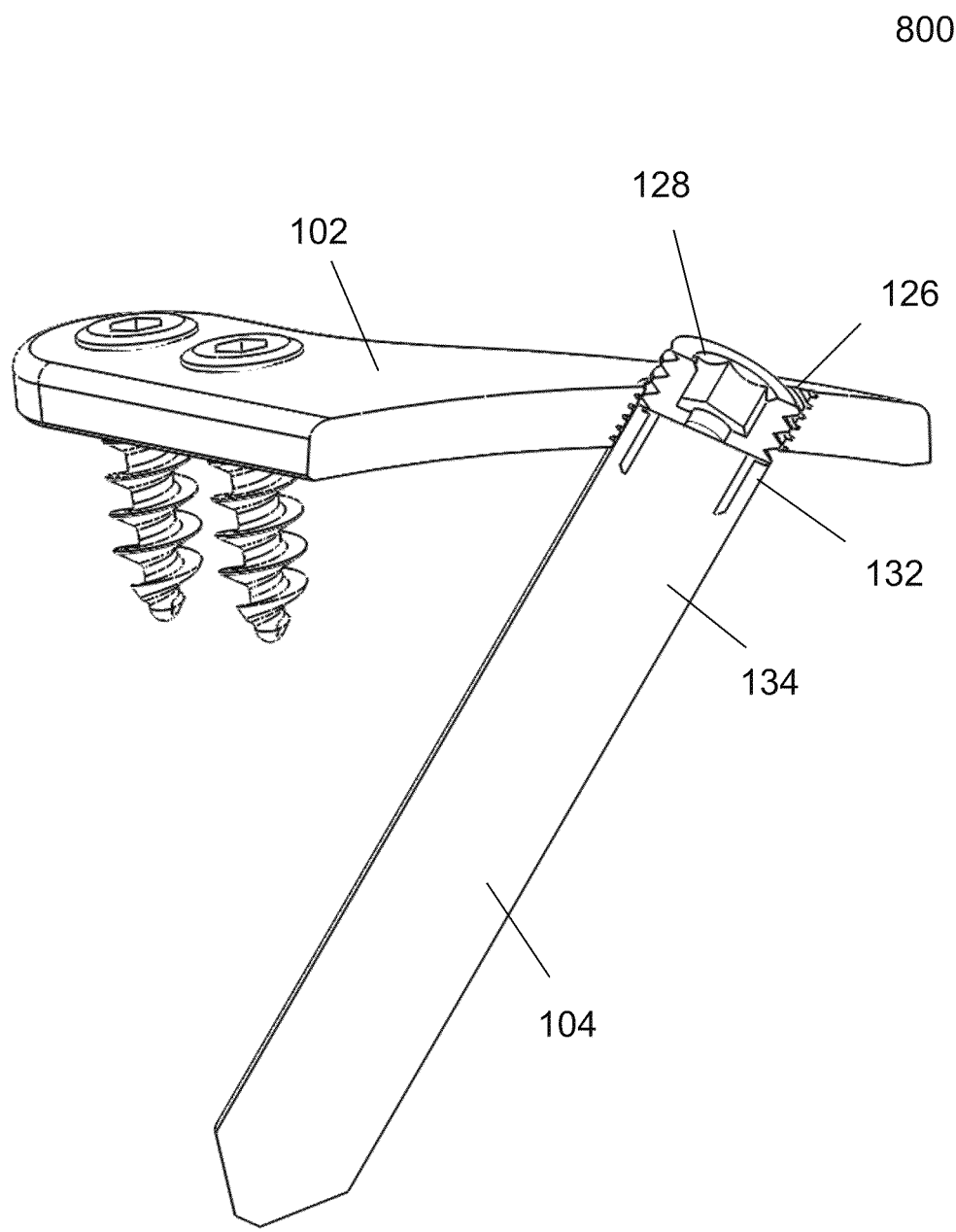
FIG. 8 depicts a cross-section view of the plate and dowel, in accordance with an embodiment of the present disclosure.

FIG. 8 depicts a cross-section view of the plate and dowel, in accordance with an embodiment of the present disclosure. FIG. 8 depicts a cross-section view of an assembled hybrid plate 800. In particular, the cross-section view illustrates a position of locking screw 128 after locking screw 128 has been inserted into a receiving chamber 134 of dowel 104 through top side 132 of dowel 104 and after locking screw 128 has been screwed and engages with the internal threads of dowel hole 126 of plate 102.

Figure 9:
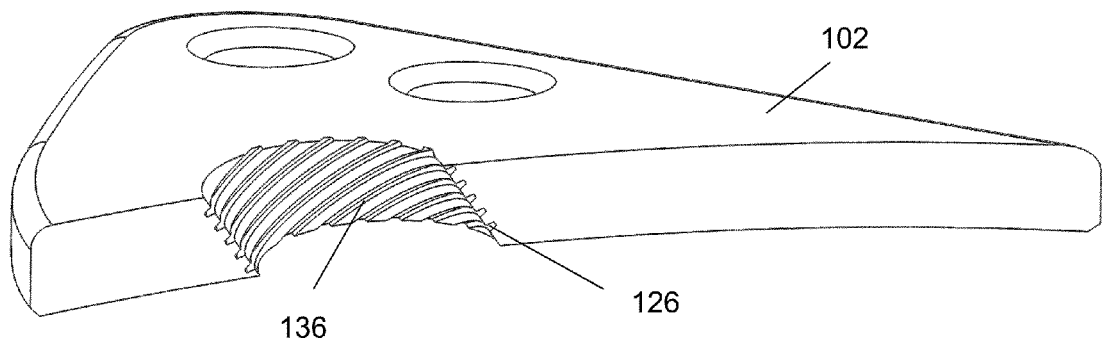
FIG. 9 depicts a cross section view of the plate, in accordance with an embodiment of the present disclosure.

FIG. 9 depicts a cross section view of the plate, in accordance with an embodiment of the present disclosure. Plate 102, as shown, in a cross section view, provides a detailed view of dowel hole 126, and in particular, internal threads 136 for engaging with locking screw 128.

Figure 10:
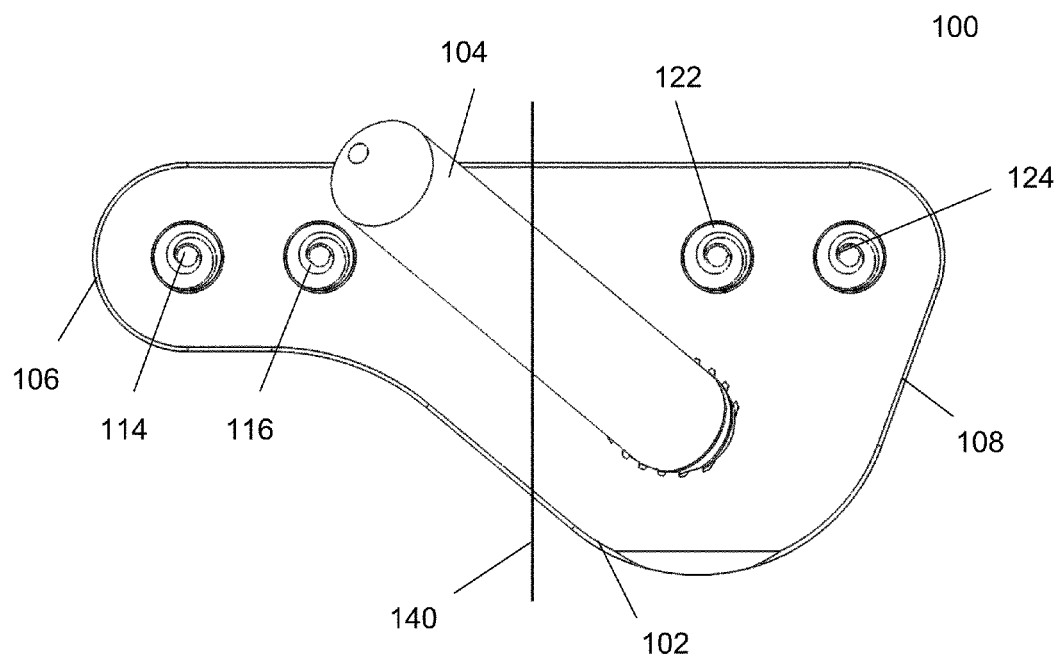
FIG. 10 depicts an under side view of the plate, in accordance with an embodiment of the present disclosure.

FIG. 10 depicts an under side view of the plate, in accordance with an embodiment of the present disclosure. FIG. 10 depicts a under side view of an assembled hybrid plate 100. Screws 114, 116, 122, and 124 have already been screwed into a first biological segment and a second biological segment. First plate portion 106 as shown is on a first side of joining plane 140 and second plate portion 108 is on a second side of joining plane 140. Joining plane 140, as depicted in FIG. 10 as a solid line representing a plane where the first biological segment and second biological segment are to be joined together. As shown dowel 104, which has already been inserted into the first biological segment and second biological segment, crosses joining plane 140.

Figure 11:
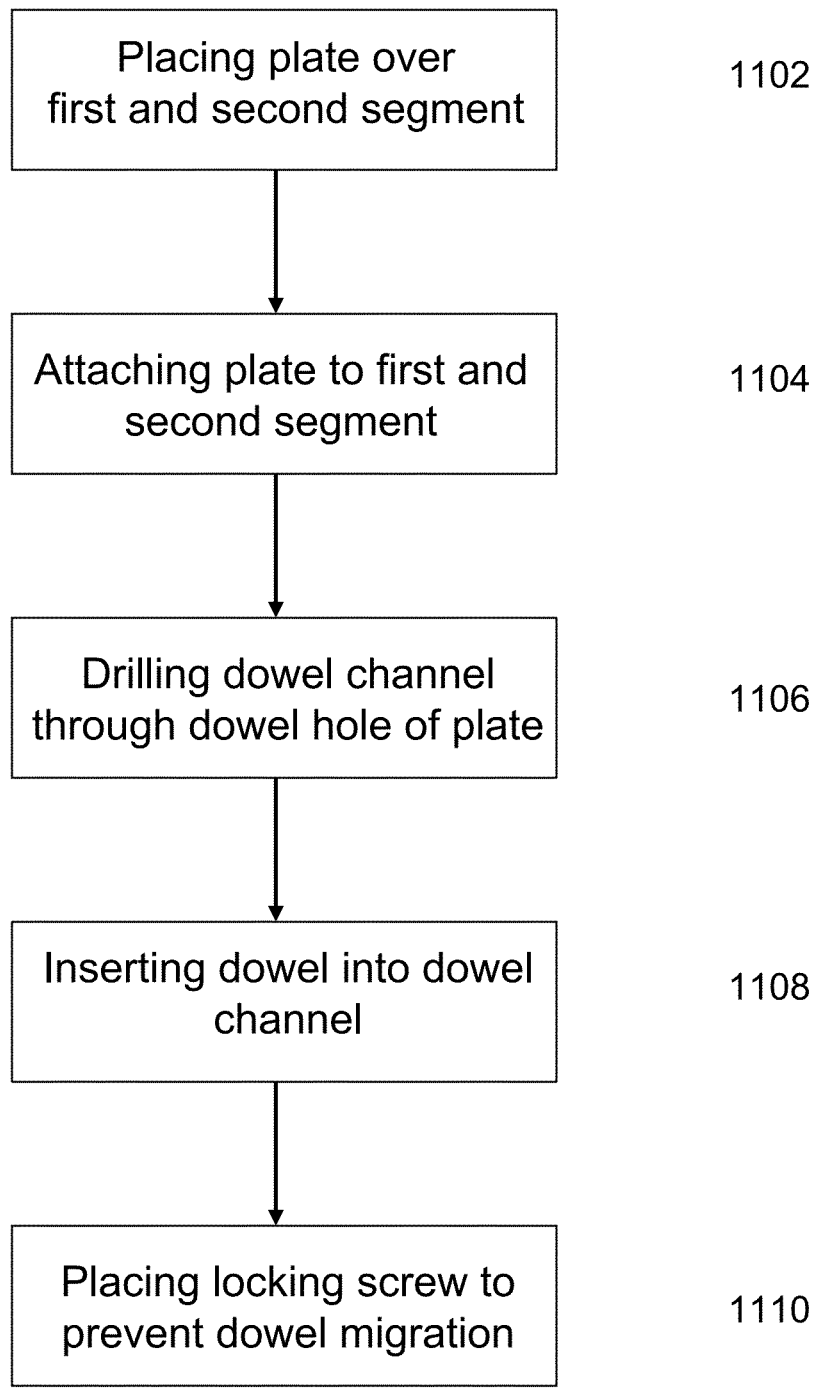
FIG. 11 depicts an exemplary process for applying an assembled hybrid plate to biological elements, in accordance with an embodiment of the present disclosure.

FIG. 11 depicts an exemplary process for applying an assembled hybrid plate to biological elements, in accordance with an embodiment of the present disclosure. A process or method for joining biological elements may begin at 1102, where a plate is placed over a first segment and a second segment. This may include placing a first plate portion over the first segment and a second plate portion over the second segment.

At 1104, the plate is attached to the first segment and the second segment. Attaching the plate to the first segment and the second segment includes inserting at least one screw into at least one hole of the plate. Each of the at least one screw may be screwed into a corresponding at least one hole of the plate such that the plate fastens or attaches to both the first segment and the second segment.

At 1106, a dowel channel is drilled thru a dowel hole of the plate. A drill bit is inserted thru the dowel hole of the plate. The drill bit is drilled thru the dowel hole and into the first segment and the second segment to form a dowel channel. The dowel channel crosses a joining plane of the first segment and the second segment. After drilling, the drill bit is removed.

At 1108, a dowel is inserted into the dowel channel, where the dowel crosses the joining plane of the first segment and the second segment. The dowel is inserted thru the dowel channel until the dowel is implanted in both the first segment and the second segment.

At 1110, a locking screw is placed on a top side of the dowel to lock the dowel in place. More specifically, the locking screw is placed within a receiving chamber on the top side of the dowel. The locking screw is then screwed into the dowel and the plate, and while screwing, the locking screw engages with internal threads of the dowel hole to lock the dowel to the plate.

Figure 12:
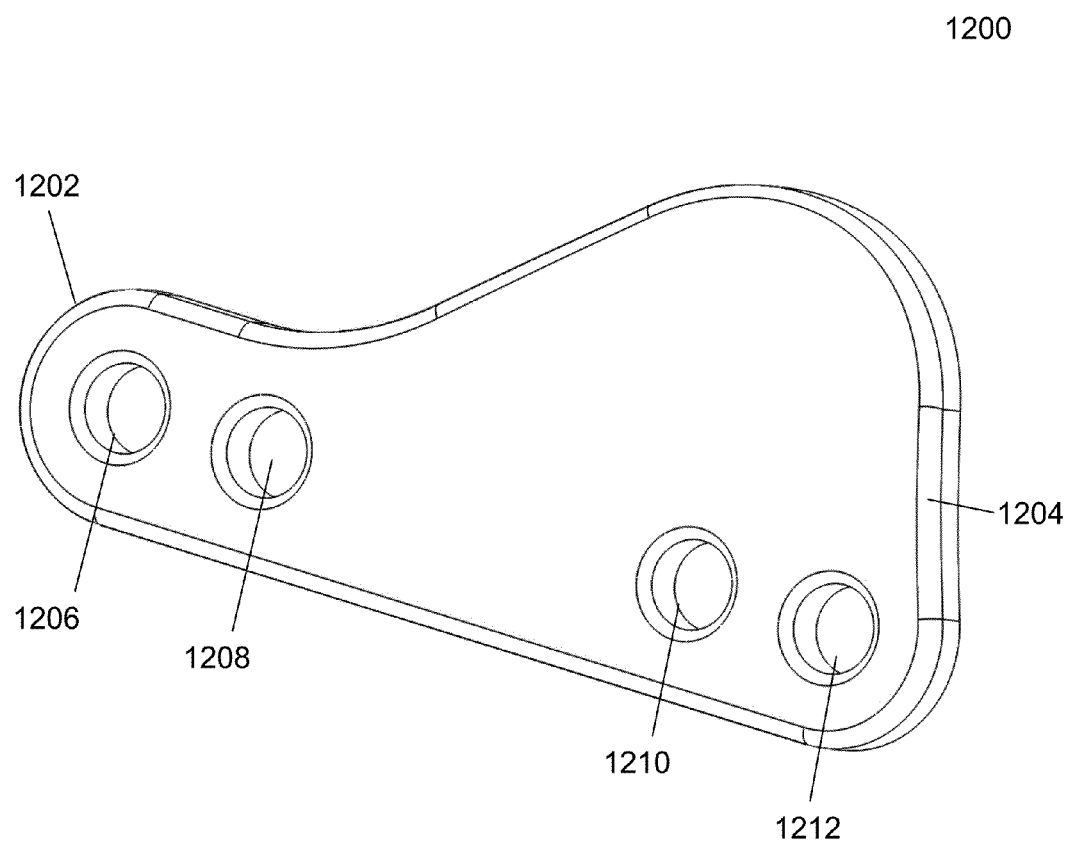
FIG. 12 depicts an exemplary perspective view of a plate, in accordance with an embodiment of the present arrangement.

FIG. 12 depicts an exemplary perspective view of a plate, in accordance with an embodiment of the present arrangement. A solid plate 1200 is depicted by FIG. 12. The solid plate comprises a first plate portion 1202 and a second plate portion 1204. The first plate portion 1202 includes two holes 1206 and 1208 for receiving screws that may attach plate 1200 to a first biological segment. The second plate portion 1204 includes two holes 1210 and 1212 for receiving screws that may attach plate 1200 to a second biological segment. While two holes are shown in each plate portion, one skilled in the art may contemplate a plate 1200 which includes more or less holes than currently shown by FIG. 12.

Figure 13:
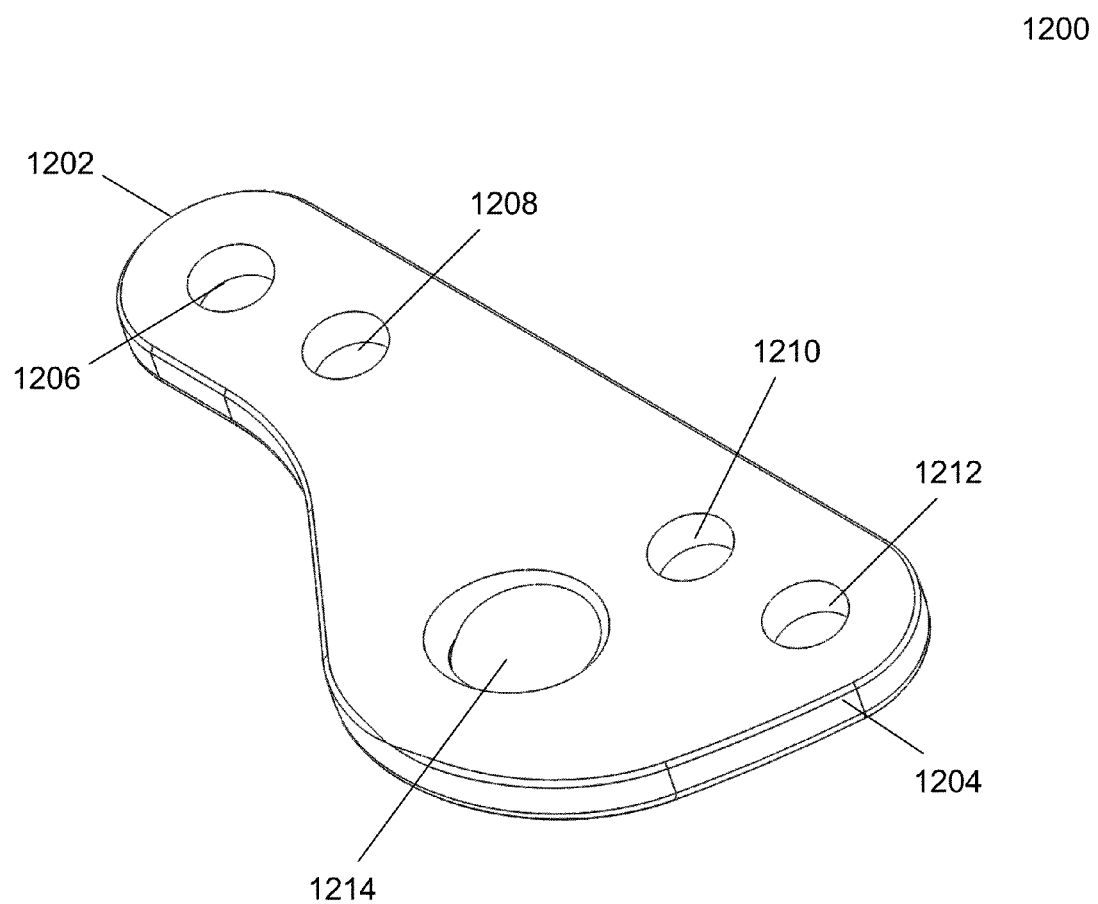
FIG. 13 depicts an exemplary perspective view of a plate, in accordance with an embodiment of the present arrangement.

FIG. 13 depicts an exemplary perspective view of a plate, in accordance with an embodiment of the present arrangement. FIG. 13 shows an underside view of plate 1200. Second plate portion 1204 as shown includes a dowel slot 1214. Dowel slot 1214 is configured to receive a top end of a dowel to hold a dowel in place. Plate 1200 may be utilized after a dowel has been inserted into a first biological segment and a second biological segment. After insertion of the dowel, plate 1200 may be placed atop the dowel such that the dowel mates with dowel slot 1214. In this manner, plate 1200 serves to hold the dowel in place to prevent movement of the dowel with respect to plate 1200. Plate 1200 serves as an anti-back out place.

Accordingly, a dowel is inserted into a first biological segment and a second biological segment. Plate 1200 is applied to the dowel such that the dowel is received by dowel slot 1214, which keeps the dowel from migrating or moving with respect to plate 1200. Screws are then inserted thru holes 1206, 1208, 1210, and 1212 to further hold plate 1200 in place atop a first biological segment and a second biological segment, as well as provide additional stability to the dowel.

Figure 14:
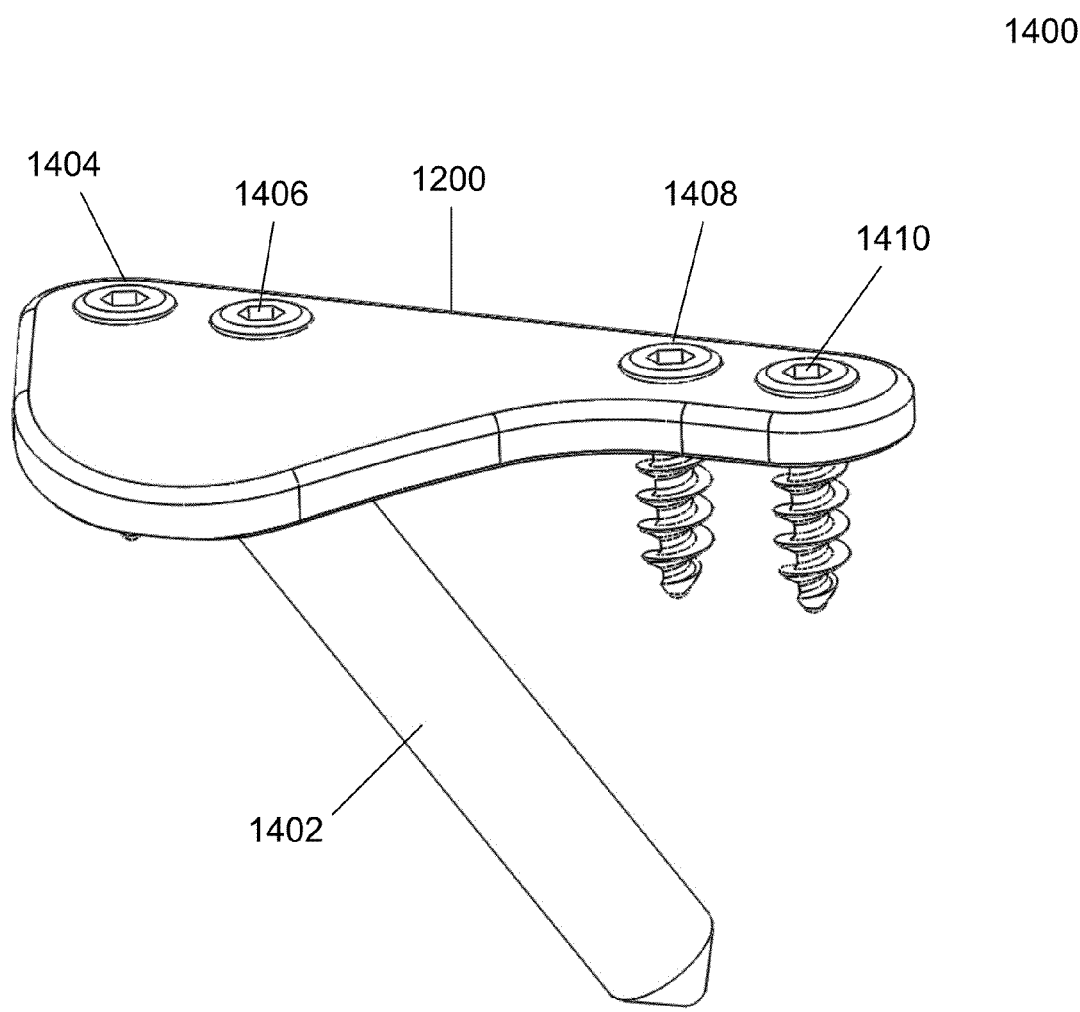
FIG. 14 depicts an exemplary perspective view of an assembled hybrid plate, in accordance with an embodiment of the present arrangement.

FIG. 14 depicts an exemplary perspective view of an assembled hybrid plate, in accordance with an embodiment of the present arrangement. Assembled hybrid plate 1400 comprises plate 1200 as shown in FIGS. 12 and 13, and dowel 1402. Assembled hybrid plate 1400 is shown in a fully assembled state after dowel 1402 has been inserted at an oblique angle through a first biological segment and a second biological segment. After dowel 1402 is inserted, plate 1200 is placed atop dowel 1402 such that dowel slot 1214 receives a top of dowel 1402. Thereafter, screws 1404, 1406, 1408, and 1410 are applied to attach plate 1200 to a first biological segment and a second biological segment. Dowel 1402 is inserted such that dowel 1402 crosses a joining plane of the first biological segment and the second biological segment.

Figure 15:
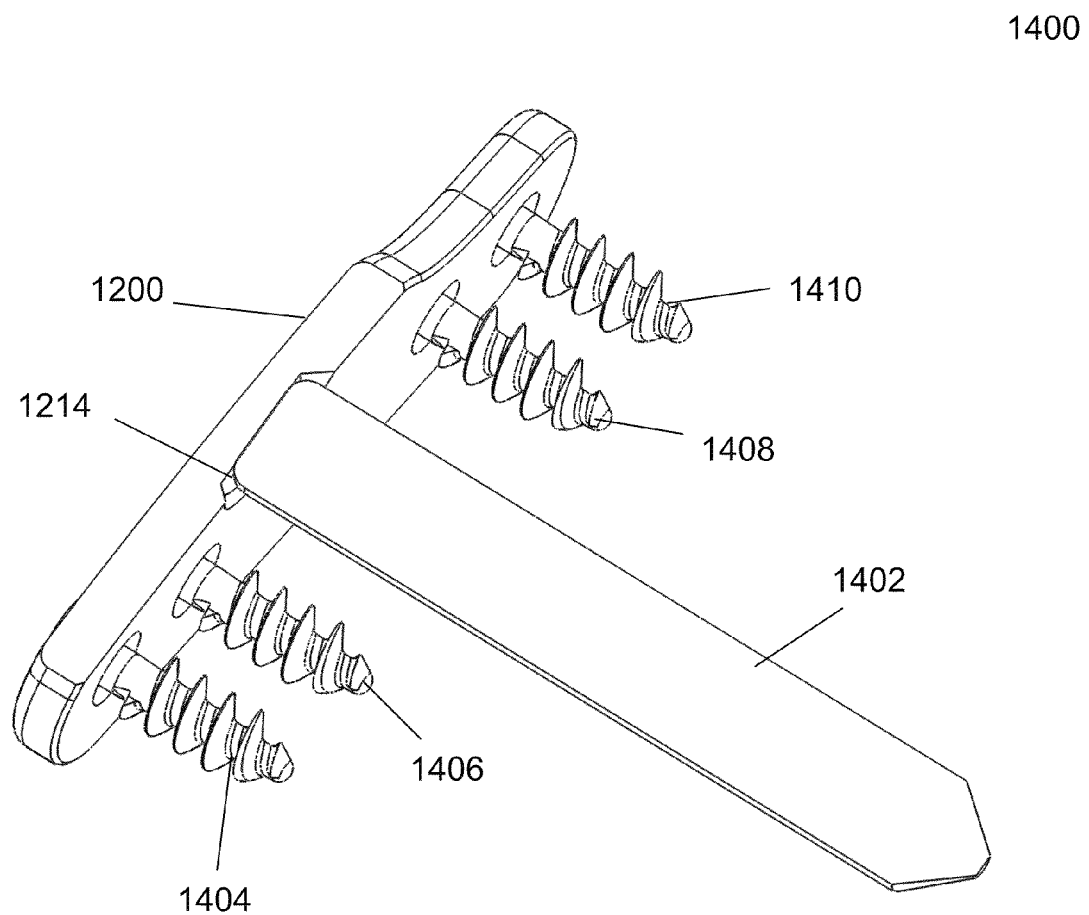
FIG. 15 depicts an exemplary perspective view of an assembled hybrid plate, in accordance with an embodiment of the present arrangement.

FIG. 15 depicts an exemplary perspective view of an assembled hybrid plate, in accordance with an embodiment of the present arrangement. FIG. 15 shows assembled hybrid plate 1400 from a perspective which shows dowel slot 1214 which has received a top end 1502 of dowel 1402.

Figure 16:
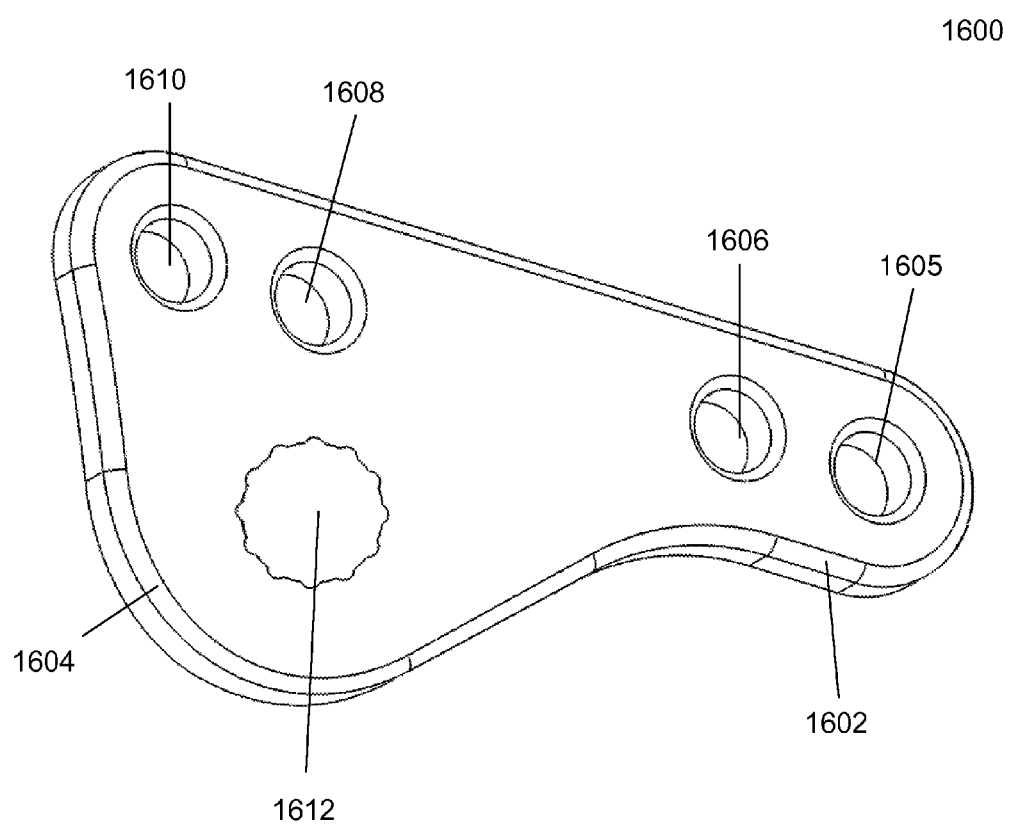
FIG. 16 depicts an exemplary perspective view of a plate with a splined or tapered surface to a dowel hole, in accordance with an embodiment of the present arrangement.

FIG. 16 depicts an exemplary perspective view of a plate with a splined or tapered surface to a dowel hole, in accordance with an embodiment of the present arrangement. Plate 1600, as shown, comprises a first plate portion 1602 and a second plate portion 1604. First plate portion 1602 comprises holes 1605 and 1606 for receiving screws to secure plate 1600 to a first biological segment. Second plate portion 1604 comprises holes 1608 and 1610 for receiving screws to secure plate 1600 to a second biological segment. Second plate portion 1604 also includes dowel hole 1612, which may include a splined or tapered surface around the circumference of the hole for receiving a dowel and thereby preventing the dowel from migration. The dowel may be tapered at an end and interlock with the splined or tapered surface, thus providing an anti-migration feature. The dowel may be hammered into place.

Figure 17:
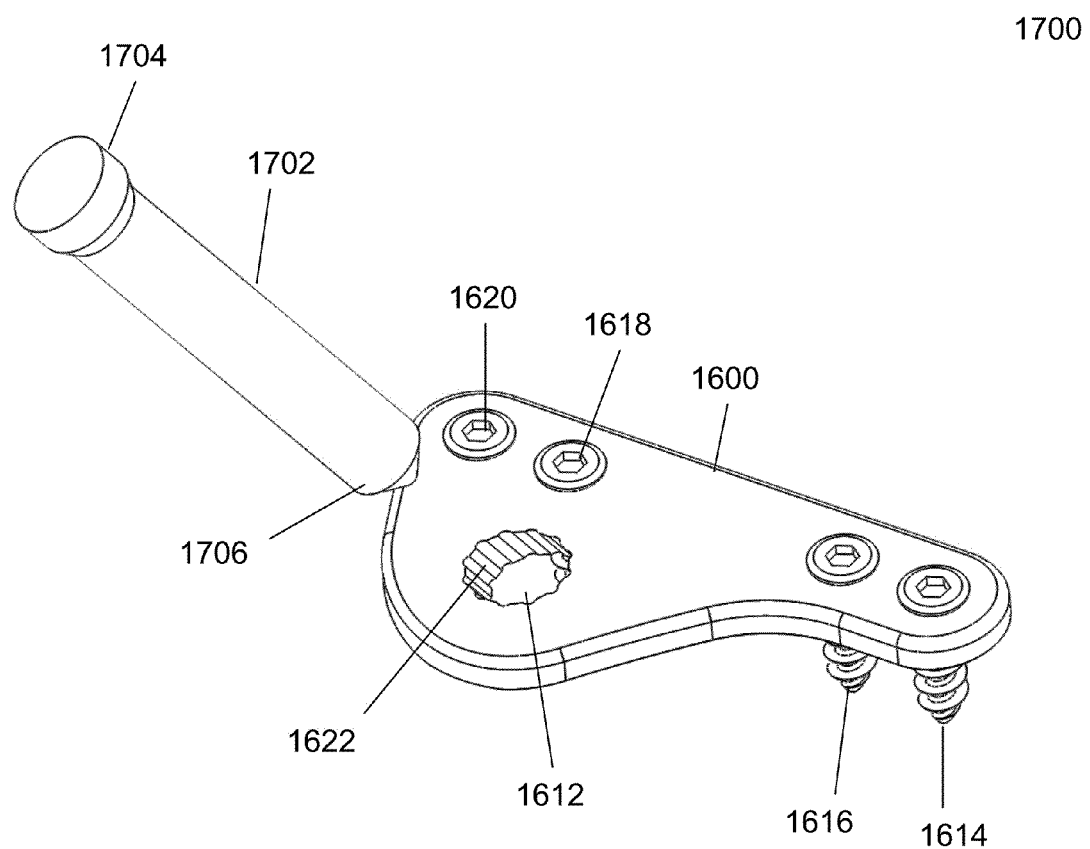
FIG. 17 depicts an exemplary perspective view of a plate with a splined or tapered surface to a dowel hole, in accordance with an embodiment of the present arrangement.

FIG. 17 depicts an exemplary perspective view of a plate with a splined or tapered surface to a dowel hole, in accordance with an embodiment of the present arrangement. FIG. 17 shows plate 1200 after screws 1614, 1616, 1618, and 1620 have been applied to attach plate 1600 to a first biological segment and a second biological segment. The splined or tapered surface of dowel hole 1612 may be observed for receiving dowel 1702 and holding dowel 1702 in place with respect to plate 1600. After plate 1600 has been secured by screws, dowel 1702 may he hammered through dowel hole 1612 such that dowel 1702 inserts into the first biological segment and the second biological segment. Dowel 1702 is hammered into the first biological segment and the second biological segment such that a tapered end 1706 of dowel 1702 penetrates the first biological segment and the second biological segment. Dowel 1702 may be hammered from a top end 1704 of dowel 1702 thru dowel hole 1612, and thru the first biological segment and the second biological segment such that dowel 1702 crosses a joining plane of the first biological segment and the second biological segment.

Figure 18:
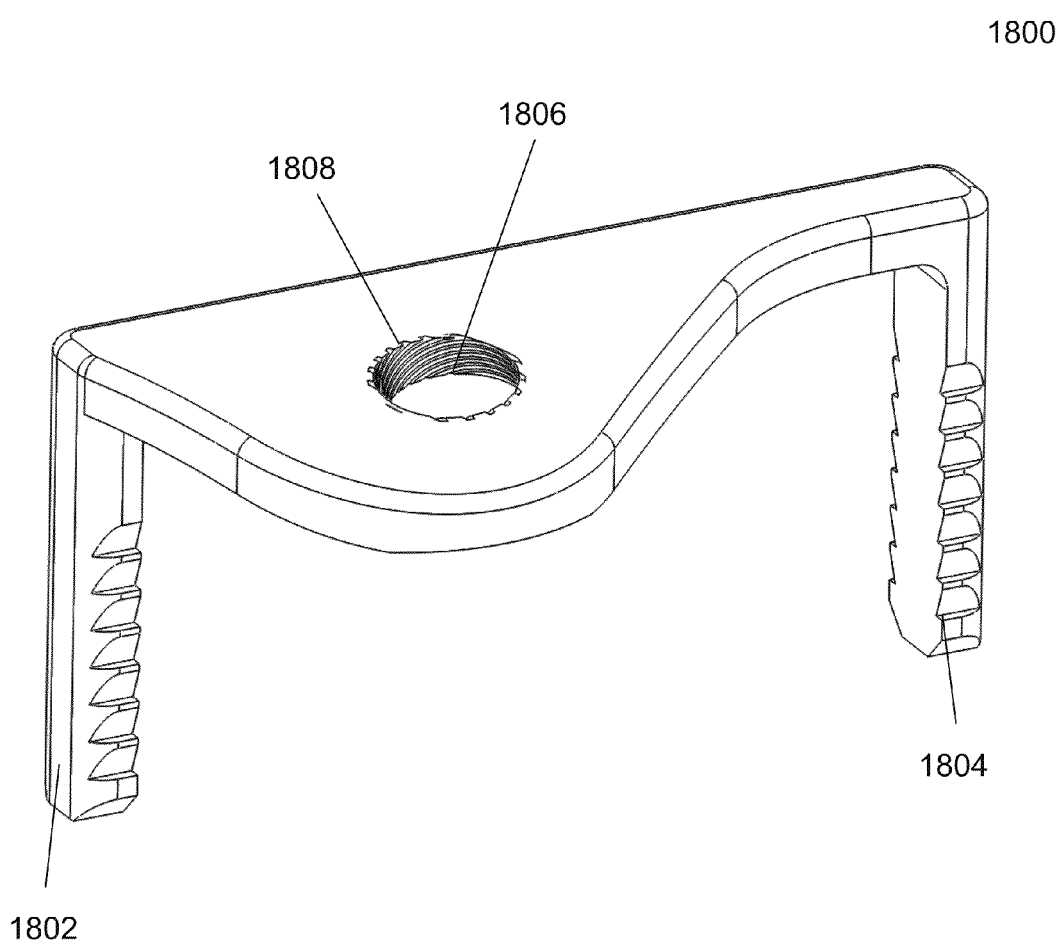
FIG. 18 depicts an exemplary perspective view of a plate including staple holding elements, in accordance with an embodiment of the present arrangement.

FIG. 18 depicts an exemplary perspective view of a plate including staple holding elements, in accordance with an embodiment of the present arrangement. Plate 1800, as shown, comprises a pair of holding elements 1802 and 1804. Holding elements 1802 and 1804 are configured for insertion into a first biological segment and a second biological segment, respectively, to attach plate 1800 to the biological segments. Holding elements 1802 and 1804 may be, for example, staple type holding means. Plate 1800 further includes dowel hole 1806 for receiving a dowel which is to be inserted thru dowel hole 1806 and into the first biological segment and the second biological segment such that the dowel crosses a joining plane of the first biological segment and the second biological segment. Dowel hole 1806 includes internal threads 1808, which are adapted to engage with a locking screw that may be placed atop a dowel in order to further lock the dowel to the plate and ensure that the dowel does not migrate and is held in place with respect to the plate.

Figure 19:
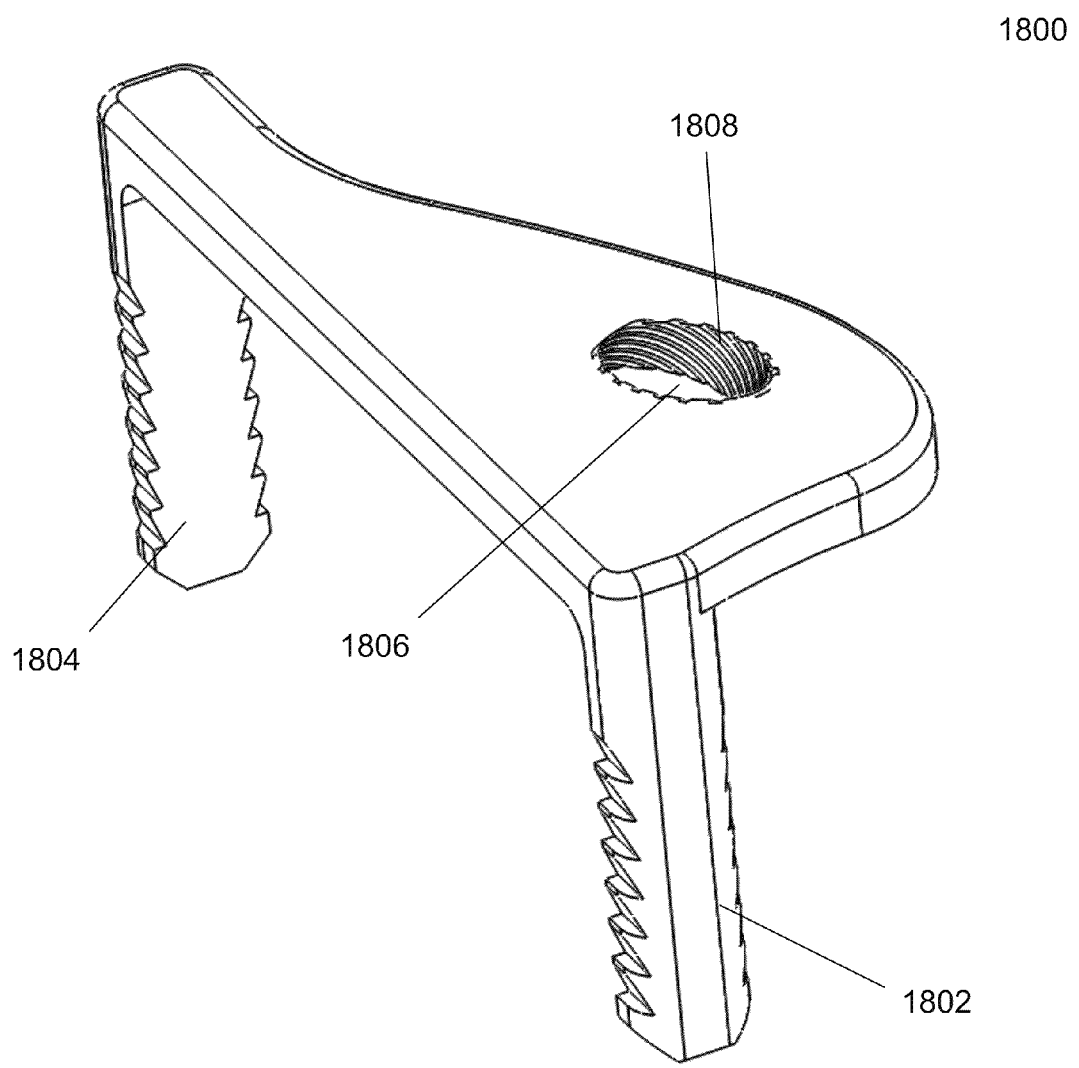
FIG. 19 depicts an exemplary perspective view of a plate including staple holding elements, in accordance with an embodiment of the present arrangement.

FIG. 19 depicts an exemplary perspective view of a plate including staple holding elements, in accordance with an embodiment of the present arrangement. FIG. 19 provides a different perspective view of plate 1800 as shown in FIG. 18. Plate 1800 is placed atop a first biological segment and second biological segment. Using an attachment device, such as a stapling mechanism, plate 1800 is applied to the first biological segment and the second biological segment such that holding element 1802 attaches to the first biological segment and holding element 1804 attaches to the second biological segment. Once plate 1800 is secured to the first biological segment and the second biological segment, a dowel may be inserted thru dowel hole 1806 after a dowel channel has been drilled thru dowel hole 1806 and thru the first biological segment and the second biological segment.

Figure 20:
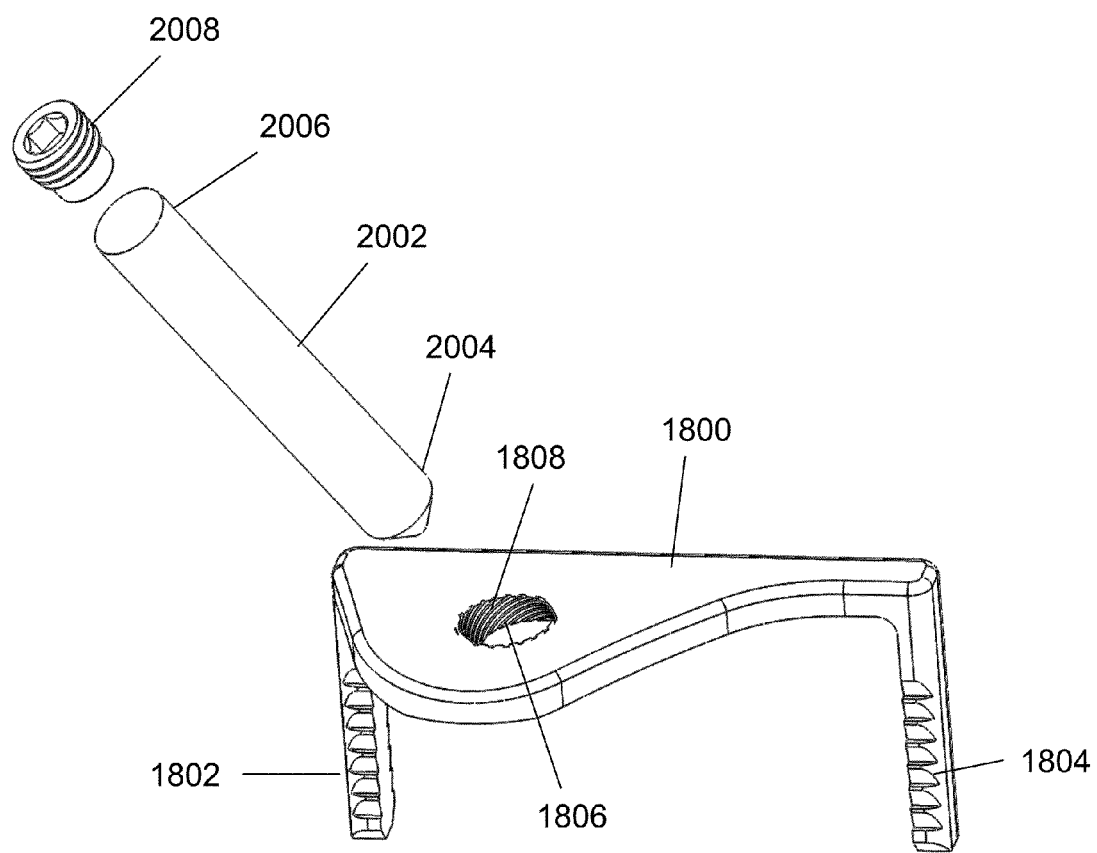
FIG. 20 depicts an exemplary perspective view of a plate including staple holding elements, in accordance with an embodiment of the present arrangement.

FIG. 20 depicts an exemplary perspective view of a plate including staple holding elements, in accordance with an embodiment of the present arrangement. Plate 1800 is shown, as well as dowel 2002 which is to be inserted thru dowel hole 1806. Once plate 1800 is attached to the first biological segment and the second biological segment, dowel 2002 is inserted thru hole 1806, where dowel 2002 crosses a joining plane of the first biological segment and the second biological segment. Dowel 2002 is inserted where a tapered or bottom end 2004 engages the first biological segment and the second biological segment as it is inserted. Once inserted, a top end 2006 of dowel 2002 may receive a locking screw 2008. Locking screw 2008 may be screwed into dowel hole 1806 where locking screw 2008 engages the internal threads 1808 of dowel hole 1806. Engaging the internal threads facilitates a locking of dowel 2002 with respect to plate 1800 to ensure that dowel 2002 does not migrate or move.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by patent law. It is to be understood that the embodiments show and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A system for joining biological elements, comprising:
   a plate defining a first longitudinal side and comprising:
   a first portion comprising at least one hole; and
   a second portion comprising at least one hole and at least one dowel hole with internal threads, the second portion defining a lateral width measured from the first longitudinal side that is greater than a lateral width of the first portion;
   at least one dowel extending from the at least one dowel hole and including a receiving chamber on a top side thereof, wherein the at least one dowel is angled longitudinally toward the first portion, angled laterally toward the first longitudinal side of the plate, and extends across a midline of the lateral width of the second portion; and
   at least one locking screw configured to mate within the receiving chamber of the at least one dowel and engage the internal threads of the at least one dowel hole to lock the at least one dowel in place.

2. The system of claim 1, wherein the first portion is configured to be placed over a first segment and the second portion is configured to be placed over a second segment.

3. The system of claim 1, further comprising:
   at least one first screw for insertion into the at least one hole of the first portion and at least one second screw for insertion into the at least one hole of the second portion, wherein the at least one first screw and the at least one second screw may be screwed into the at least one hole of the first portion and the second portion, respectively, to fasten the plate to a first segment and a second segment.

4. The system of claim 1, wherein the at least one dowel is configured to be implanted in both a first segment and a second segment.

5. The system of claim 4, wherein the first segment and the second segment are bone segments or joint segments.

6. The system of claim 1, wherein the plate and the at least one dowel form a single constructive construct for joining.

7. The system of claim 1, wherein the at least one dowel may be at least one of: round, polygonal, or splined in cross section.

8. The system of claim 1, wherein the at least one dowel is at least one of: bone, bone scaffold, mineral, ceramic, metal matrix, including stem cells, or including autologous material.

9. The system of claim 1, wherein the first longitudinal side of the plate is defined by the first portion and the second portion and is substantially linear.

10. The system of claim 1, wherein the first portion and the second portion are substantially aligned along the first longitudinal side of the plate.

11. The system of claim 1, wherein the at least one dowel crosses a midline of a longitudinal length of the plate.

12. The system of claim 1, wherein the at least one dowel crosses a midline of a longitudinal length of the second portion of the plate.

13. The system of claim 1, wherein the at least one dowel crosses a midline of the lateral width of the first portion.

14. The system of claim 1, wherein the at least one dowel extends laterally past the first longitudinal side of the plate.

15. The system of claim 1, wherein the at least one hole of the first portion and the at least one hole of the second portion are proximate to the first longitudinal side, and the at least one dowel hole is proximate to a second longitudinal side of the plate that opposes the first longitudinal side.

16. The system of claim 15, wherein the first longitudinal side of the plate is substantially linear and the second longitudinal side of the plate is substantially non-linear.

17. A system for joining biological elements, comprising:
a plate defining a first longitudinal side and comprising:
a first portion comprising at least one hole; and
a second portion comprising at least one hole and at least one dowel hole and defining a lateral width measured from the first longitudinal side that is greater than a lateral width of the first portion;
at least one dowel extending from the at least one dowel hole, wherein the at least one dowel is angled longitudinally toward the first portion, angled laterally toward the first longitudinal side of the plate, and extends across a midline of the lateral width of the second portion;
at least one locking screw configured for mating with a top side of the at least one dowel to lock the at least one dowel in place; and
a drill bit for insertion thru the at least one dowel hole, wherein the drill bit may be drilled thru the at least one dowel hole and into a first segment and a second segment to form at least one dowel channel crossing a joining plane of the first segment and the second segment.

18. An apparatus for joining biological elements, comprising:
a first portion comprising at least one hole and defining a first lateral width;
a second portion comprising at least one hole and at least one dowel hole, the second portion defining a second lateral width that is greater than the first lateral width of the first portion; and
a dowel extending from the at least one dowel hole longitudinally toward the first portion and laterally across a midline of the second lateral width of the second portion such that the dowel is configured to cross a joining plane of a first segment and a second segment, and
wherein the at least one dowel hole comprises internal threads for engaging with at least one locking screw mating with a top side of the dowel to lock the dowel in place.

19. The apparatus of claim 18, wherein the first portion is configured to be placed over the first segment and the second portion is configured to be placed over the second segment.

20. The apparatus of claim 18, wherein the at least one hole of the first portion and the second portion are configured to receive at least one screw to fasten the plate to the first segment and the second segment.

21. The apparatus of claim 18, wherein the at least one dowel hole is configured to receive a drill bit that may be drilled thru the at least one dowel hole and into the first segment and the second segment to form at least one dowel channel crossing the joining plane of the first segment and the second segment.

22. The apparatus of claim 18, wherein the dowel comprises a receiving chamber on a top side of the dowel.

23. The apparatus of claim 18, wherein the first portion, the second portion and the dowel form a single constructive construct for joining.

24. The apparatus of claim 18, wherein the first segment and the second segment are bone segments or joint segments.

25. The apparatus of claim 18, wherein the dowel may be at least one of round, polygonal, or splined in cross section.

26. The apparatus of claim 18, wherein the dowel is fabricated from at least one of bone, bone scaffold, mineral, ceramic, metal matrix, including stem cells, or including autologous material.

27. A system for joining biological elements, comprising:
a plate defining a first longitudinal side and comprising:
a first portion comprising at least one retention element; and
a second portion comprising at least one retention element and at least one dowel hole and defining a second lateral width measured from the first longitudinal side that is wider than a first lateral width of the first portion; and
at least one dowel extending from the at least one dowel hole configured for insertion into a corresponding dowel channel, wherein the at least one dowel extends longitudinally toward the first portion and laterally across a midline of the second lateral width of the second portion such that the dowel is configured to contact both a first segment and a second segment.

28. The system of claim 27, wherein the at least one retention element is at least one of: a screw, or a flexible member.

29. The system of claim 28, wherein the flexible member is a suture.

30. The system of claim 27, wherein the at least one dowel is retained in place within the corresponding dowel hole by mechanical contact with the plate.

31. The system of claim 27, further comprising:
an anti-migration feature for engagement with the at least one dowel at the corresponding dowel hole.

32. The system of claim 31, wherein the anti-migration feature is at least one of a set screw, a spline interfering with at least a portion of a dowel, or a tapered fit.

33. A system for joining biological elements, comprising:
a plate comprising:
a first portion comprising at least one retention feature and defining a first lateral width; and
a second portion comprising at least one retention feature and at least one dowel contact point, the second portion defining a second lateral width that is greater than the first lateral width of the first portion; and
at least one dowel extending from and secured by the at least one dowel contact point configured for insertion thru a dowel channel, the at least one dowel extending longitudinally toward the first portion and laterally across a midline of the second lateral width of the second portion such that the dowel is configured to contact a first segment and a second segment.

34. A system for joining biological elements, comprising:
a plate defining a first longitudinal side and comprising:
- a first portion comprising at least one hole; and
- a second portion comprising at least one hole and at least one dowel hole and defining a lateral width measured from the first longitudinal side that is greater than a lateral width of the first portion;

at least one dowel extending from the at least one dowel hole, wherein the at least one dowel is angled longitudinally toward the first portion, angled laterally toward the first longitudinal side of the plate, and extends across a midline of the lateral width of the second portion; and at least one locking screw configured for mating with a top side of the at least one dowel to lock the at least one dowel in place, wherein the at least one hole of the first portion and the at least one hole of the second portion are non-threaded, and the at least one dowel hole includes internal threads.

35. The system of claim 34, wherein the at least one locking screw is placed into a receiving chamber on the top side of the at least one dowel, and the at least one locking screw is configured to engage with internal threads of the at least one dowel hole to lock the at least one dowel to the plate.

36. The system of claim 34, further comprising:
at least one first screw for insertion into the at least one hole of the first portion and at least one second screw for insertion into the at least one hole of the second portion, wherein the at least one first screw and the at least one second screw may be screwed into the at least one hole of the first portion and the second portion, respectively, to fasten the plate to a first segment and a second segment.

37. The system of claim 34, wherein the at least one dowel is configured to be implanted in both a first segment and a second segment.

38. The system of claim 37, wherein the first segment and the second segment are bone segments or joint segments.

39. The system of claim 34, wherein the plate and the at least one dowel form a single constructive construct for joining elements.

40. The system of claim 34, wherein the first longitudinal side of the plate is defined by the first portion and the second portion and is substantially linear.

41. The system of claim 34, wherein the first portion and the second portion are substantially aligned along the first longitudinal side of the plate.

42. The system of claim 34, wherein the dowel crosses a midline of a longitudinal length of the plate.

43. The system of claim 34, wherein the dowel crosses a midline of a longitudinal length of the second portion of the plate.

44. The system of claim 34, wherein the dowel crosses a midline of the lateral width of the first portion.

45. The system of claim 34, wherein the dowel extends laterally past the first longitudinal side of the plate.

46. The system of claim 34, wherein the at least one hole of the first portion and the at least one hole of the second portion are proximate to the first longitudinal side, and the at least one dowel hole is proximate to a second longitudinal side of the plate that opposes the first longitudinal side.

47. The system of claim 46, wherein the first longitudinal side of the plate is substantially linear and the second longitudinal side of the plate is substantially non-linear.

48. The system of claim 34, further comprising a drill bit for insertion thru the at least one dowel hole, wherein the drill bit may be drilled thru the at least one dowel hole and into a first segment and a second segment to form at least one dowel channel crossing a joining plane of the first segment and the second segment.

49. The system of claim 34, wherein the at least one dowel extends from the at least one dowel hole such that the dowel is configured to cross a joining plane of a first segment and a second segment, and wherein the internal threads of the at least one dowel hole are configured to mate with at least one locking screw to lock the at least one dowel in place.

50. The system of claim 34, wherein each of the first portion and the second portion further comprise at least one retention element.

51. The system of claim 34, wherein the second portion further comprises at least one retention feature and at least one dowel contact point, and wherein at least one dowel extends from and is secured by the at least one dowel contact point and is configured for insertion thru a dowel channel to contact a first segment and a second segment.

* * * * *